(12) United States Patent
Atallah

(10) Patent No.: US 11,266,412 B2
(45) Date of Patent: Mar. 8, 2022

(54) VIDEO-GUIDED ENDOLUMINAL STAPLING METHOD AND SYSTEM

(71) Applicant: Osama B. Atallah, Orlando, FL (US)

(72) Inventor: Osama B. Atallah, Orlando, FL (US)

(*) Notice: Subject to any disclaimer, the term of this patent is extended or adjusted under 35 U.S.C. 154(b) by 29 days.

(21) Appl. No.: 16/273,005

(22) Filed: Feb. 11, 2019

(65) Prior Publication Data

US 2020/0093493 A1 Mar. 26, 2020

Related U.S. Application Data

(60) Provisional application No. 62/736,276, filed on Sep. 25, 2018.

(51) Int. Cl.
| | | |
|---|---|---|
| *A61B 17/115* | (2006.01) | |
| *A61B 17/072* | (2006.01) | |
| *A61B 90/00* | (2016.01) | |
| *A61B 17/11* | (2006.01) | |
| *A61B 17/00* | (2006.01) | |
| *A61B 17/34* | (2006.01) | |
| *A61B 17/04* | (2006.01) | |

(52) U.S. Cl.
CPC ........ *A61B 17/1155* (2013.01); *A61B 17/072* (2013.01); *A61B 90/37* (2016.02); *A61B 17/0469* (2013.01); *A61B 17/1114* (2013.01); *A61B 17/3417* (2013.01); *A61B 2017/00199* (2013.01); *A61B 2017/00473* (2013.01); *A61B 2017/00818* (2013.01); *A61B 2017/07257* (2013.01); *A61B 2090/0811* (2016.02)

(58) Field of Classification Search
CPC .... A61B 90/37; A61B 17/1155; A61B 17/072
See application file for complete search history.

(56) References Cited

U.S. PATENT DOCUMENTS

| | | | | |
|---|---|---|---|---|
| 3,858,577 | A * | 1/1975 | Bass | A61B 18/24 600/108 |
| 5,251,613 | A * | 10/1993 | Adair | A61B 1/00147 600/102 |
| 5,395,030 | A * | 3/1995 | Kuramoto | A61B 1/00087 227/179.1 |
| 5,860,581 | A | 1/1999 | Robertson et al. | |
| 6,796,939 | B1 * | 9/2004 | Hirata | A61B 1/00036 600/109 |
| 7,686,201 | B2 | 3/2010 | Csiky | |

(Continued)

OTHER PUBLICATIONS

Medtronic "EEA Staplers with DST Series Technology" (2016) 6 pages.

*Primary Examiner* — Nathaniel C Chukwurah
(74) *Attorney, Agent, or Firm* — Perkins Coie LLP

(57) ABSTRACT

Disclosed are devices, systems and methods for video-guided endoluminal stapling. An exemplary device includes a circular stapler that includes an anvil and a shaft, an endoscope, and one or more connectors or fasteners that hold the endoscope against the shaft of the circular stapler, wherein the anvil includes a first opening in the anvil, wherein the endoscope is positioned through the first opening, wherein the one or more connectors or fasteners allow the endoscope to move longitudinally along the shaft of the circular stapler, and wherein a section of the shaft includes a second opening that allows the endoscope to transition from an external surface of the shaft to an internal cavity of the stapler.

13 Claims, 11 Drawing Sheets

(56) References Cited

U.S. PATENT DOCUMENTS

| | | | |
|---|---|---|---|
| 8,631,991 B2* | 1/2014 | Cropper | A61B 17/0684 227/176.1 |
| 9,155,536 B1 | 10/2015 | Hausen et al. | |
| 2006/0020213 A1* | 1/2006 | Whitman | A61B 1/05 600/478 |
| 2006/0235458 A1* | 10/2006 | Belson | A61M 25/0032 606/191 |
| 2009/0192349 A1* | 7/2009 | Berguer | A61B 5/0086 600/109 |
| 2010/0084453 A1 | 4/2010 | Hu | |
| 2010/0096435 A1* | 4/2010 | Fuchs | A61B 17/1114 227/179.1 |
| 2011/0121049 A1* | 5/2011 | Malinouskas | A61B 90/98 227/175.1 |

* cited by examiner

VIDEO-GUIDED ENDOLUMINAL STAPLING METHOD AND SYSTEM

CROSS-REFERENCE TO RELATED APPLICATION

This patent document claims priority to and benefits of U.S. Provisional Patent Application No. 62/736,276 entitled "VIDEO GUIDED ENDOLUMINAL STAPLING SYSTEM AND SURGICAL ACCESS CHANNELS AS AN ADJUNCT TO STAPLERS FOR VISUALIZATION, GAS INSUFFLATION, AND MANIPULATION" and filed on Sep. 25, 2018. The entire contents of the before-mentioned patent applications are incorporated by reference as part of the disclosure of this patent document.

TECHNICAL FIELD

This document generally relates to surgical instrumentation, and more particularly to endoluminal stapling systems for surgical operations.

BACKGROUND

The endoscopy procedure uses an endoscope to examine the interior of a hollow organ or cavity of the body. Unlike many other medical imaging techniques, endoscopes are inserted directly into the organ. A key component of endoscopic surgery is surgical stapling, which provides an accurate and effective alternative to suturing. Close to $2 billion worth of surgical stapling devices were sold in the world in 2017, and revenues are expected to double by the end of 2026.

SUMMARY

Disclosed are devices, systems and methods for video-guided endoluminal stapling to be used in endoscopic procedures. In an example, this may be achieved by retrofitting a surgical circular stapler for use with a flexible or rigid endoscope.

In one aspect, a video-guided endoluminal stapling system is disclosed. The system includes a circular stapler that includes an anvil and a shaft, an endoscope, and one or more connectors or fasteners that hold the endoscope against the shaft of the circular stapler, wherein the anvil includes a first opening in the anvil, wherein the endoscope is positioned through the first opening, wherein the one or more connectors or fasteners allow the endoscope to move longitudinally along the shaft of the circular stapler, and wherein a section of the shaft includes a second opening that allows the endoscope to transition from an external surface of the shaft to an internal cavity of the stapler.

In another aspect, a system for improving endoluminal stapling is disclosed. The system includes a circular stapler comprising a shaft, an endoscope, and one or more connectors, fasteners, or guides that allow the endoscope to move longitudinally along the shaft of the circular stapler, wherein a section of the shaft or a housing of the stapler comprises an opening that allows the endoscope to transition from an external surface of the shaft to an internal cavity of the stapler.

In yet another aspect, the disclosed technology may be used to provide a method for producing a video-guided circular stapler. This method includes creating a first opening in the anvil of the circular stapler, creating, a second opening in a shaft of the circular stapler, and affixing an endoscope along a length and on a surface of the circular stapler, wherein the second opening is configured to allow the endoscope to transition from the surface to an internal cavity of the circular stapler, and the first opening is configured to allow the endoscope to transition from the internal cavity beyond an outer surface of the anvil.

In yet another aspect, the disclosed technology may be used to performing an anastomotic stapling operation using a video-guided circular stapler. This method includes inserting a shaft of a video-guided circular stapler into a first end of a tubular tissue, extending an endoscope through an opening in an anvil of the video-guided circular stapler, the opening being offset from a center of the anvil, guiding, using the endoscope, the video-guided circular stapler to a target site, firing, upon reaching the target site, the video-guided circular stapler to perform the anastomotic stapling operation, and examining, using the endoscope, a construction of the anastomotic stapling operation.

In yet another aspect. the disclosed technology may be used to provide a method for The above and other aspects and features of the disclosed technology are described in greater detail in the drawings, the description and the claims.

DETAILED DESCRIPTION

Figures 1A, 1B:
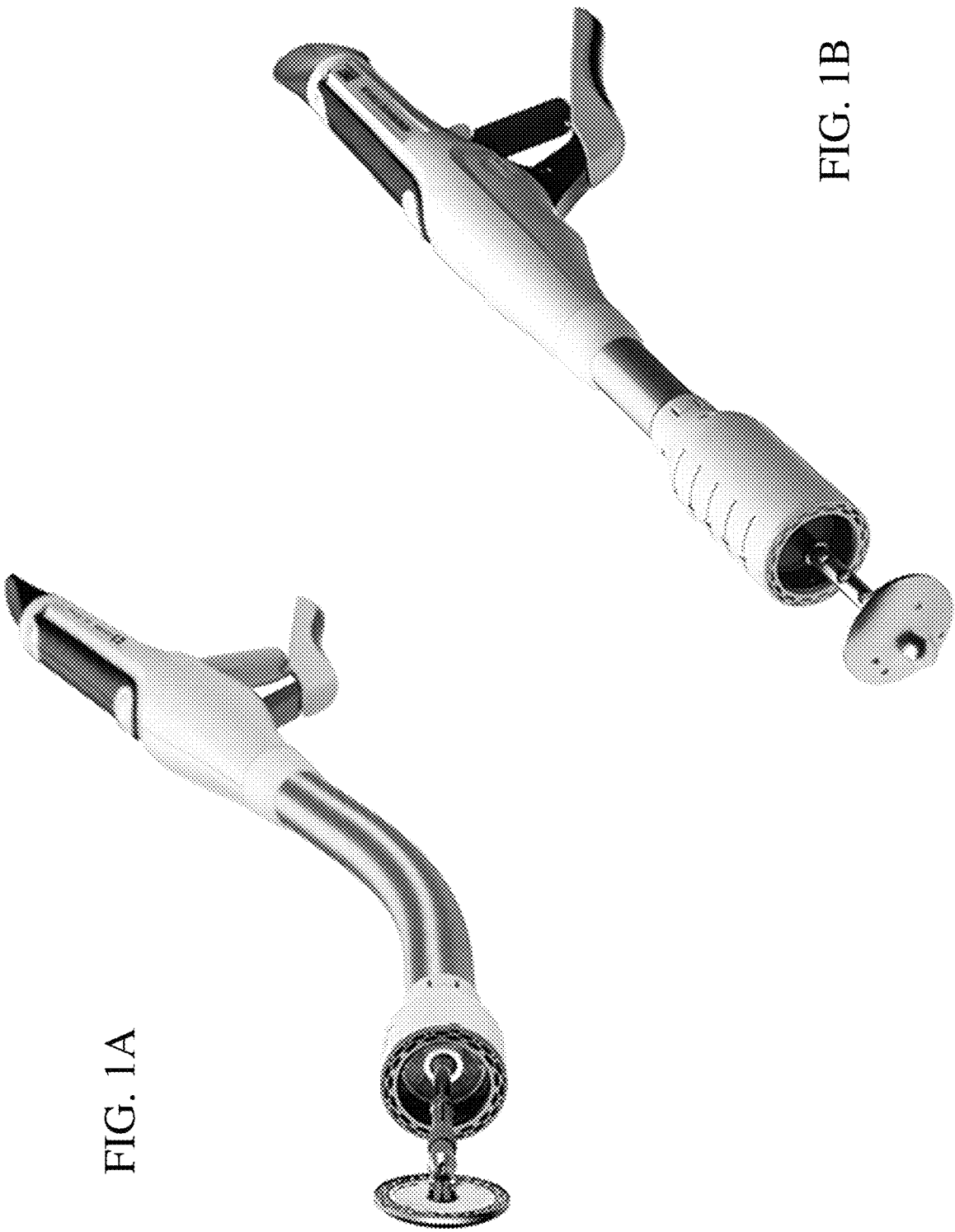
FIGS. 1A, 1B, and 1C illustrate examples of circular staplers.

Although the first recorded use of staplers in surgery occurred in 1827, wide-spread usage did not start until the development of linear staplers in the Soviet Union in the 1950's. Substantial improvements in stapling technology have been achieved, such as multi-row staple lines, switching from steel to titanium for superior biocompatibility, and most recently the introduction of powered devices. Circular staplers, illustrated in the examples in FIGS. 1A-1C, to facilitate colorectal anastomoses first emerged in surgical practice in the 1970's.

Figure 1C:
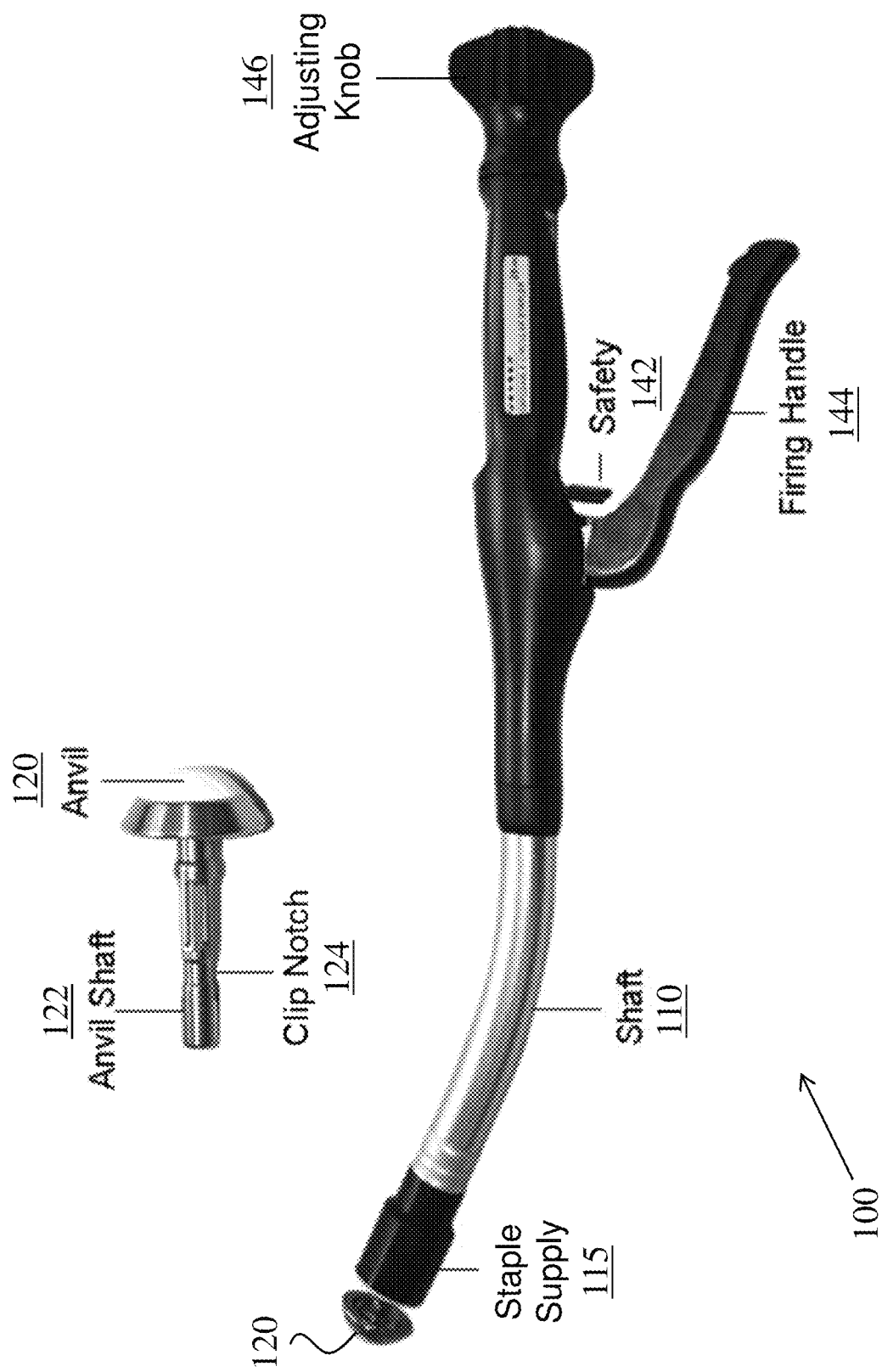

As illustrated in FIG. 1C, a typical circular stapler 100 includes an anvil 120, which serves as a base onto which the staples are impacted from the stapler supply 115, which is located at the distal end of the circular stapler 100. The anvil 120 interfaces with the shaft and the stapler supply 115 via the anvil shaft 122 and the clip notch 124 (illustrated in the inset). The shaft 110 of the circular stapler includes a safety mechanism 142 and a firing handle 144, and ends in an adjusting knob 146 at the proximate end of the circular stapler. The adjusting knob 146 is used to adjust a trocar (not shown in FIG. 1C) that allows the anvil shaft to interface with the circular stapler 100.

Generally, in the performance of a surgical anastomotic stapling operation, two pieces of lumen or tubular tissue, e.g., intestinal tissue, are attached together by a ring of staples. The two pieces of tubular tissue may be attached end to end or one piece of tubular tissue may be attached laterally around an opening formed in the side of another piece of tubular tissue. In performing the anastomosis with a circular stapler, the two pieces of tubular tissue are clamped together between an anvil provided with a circular array of staple forming grooves and a staple holder provided with a plurality of staple receiving slots arranged in a circular array in which the staples are received. A staple pusher is advanced to drive the staples into the tissue and form the staples against the anvil. Also, a circular knife is advanced to cut the excess tissue clamped between the anvil and the staple holder. As a result, a donut-shaped section of tissue is severed from each lumen and remains on the anvil shaft. The tubular tissue joined by the circular ring of staples is unclamped by advancing the anvil shaft distally to move the anvil away from the staple holder. The circular stapler is removed by pulling the anvil through the circular opening between the pieces of tubular tissue attached by the ring of staples.

One of the main advantages of a circular stapler is reliability in creating anastomoses that are resistant to leak. However, the lack of a guiding process or method continues to be an issue when using a circular stapler in rectal and rectosigmoid surgeries, as well as other part of the anatomy, such as a blood vessel, duct, or a gastrointestinal tract, where the location of interest is hidden from view. That is, once the stapler arm is inserted, it is guided to the target based on feel (e.g., using another hand) or by receiving directions based on a view from the other side.

Figure 2:
FIG. 2 illustrates an example of a video laryngoscope.

In contrast, a video laryngoscope, as illustrated in the example in FIG. 2, provides high-definition video while examining the larynx or performing an intubation. The typical laryngoscope includes built-in support for video guidance or examination, but currently such features are not available for medical stapler in general, and circular staplers in particular. As is evident from the examples shown in FIGS. 1A-1C and FIG. 2, creating a circular stapler with built-in support for video guidance or examination would require a redesign and would incur significant expense, which would normally be passed on to the consumers. Embodiments of the presently disclosed technology provide a cost-effective way to retrofit existing circular staplers to enable video-assisted guidance and examination when performing, for example, an anastomosis.

Figures 3A, 3B:
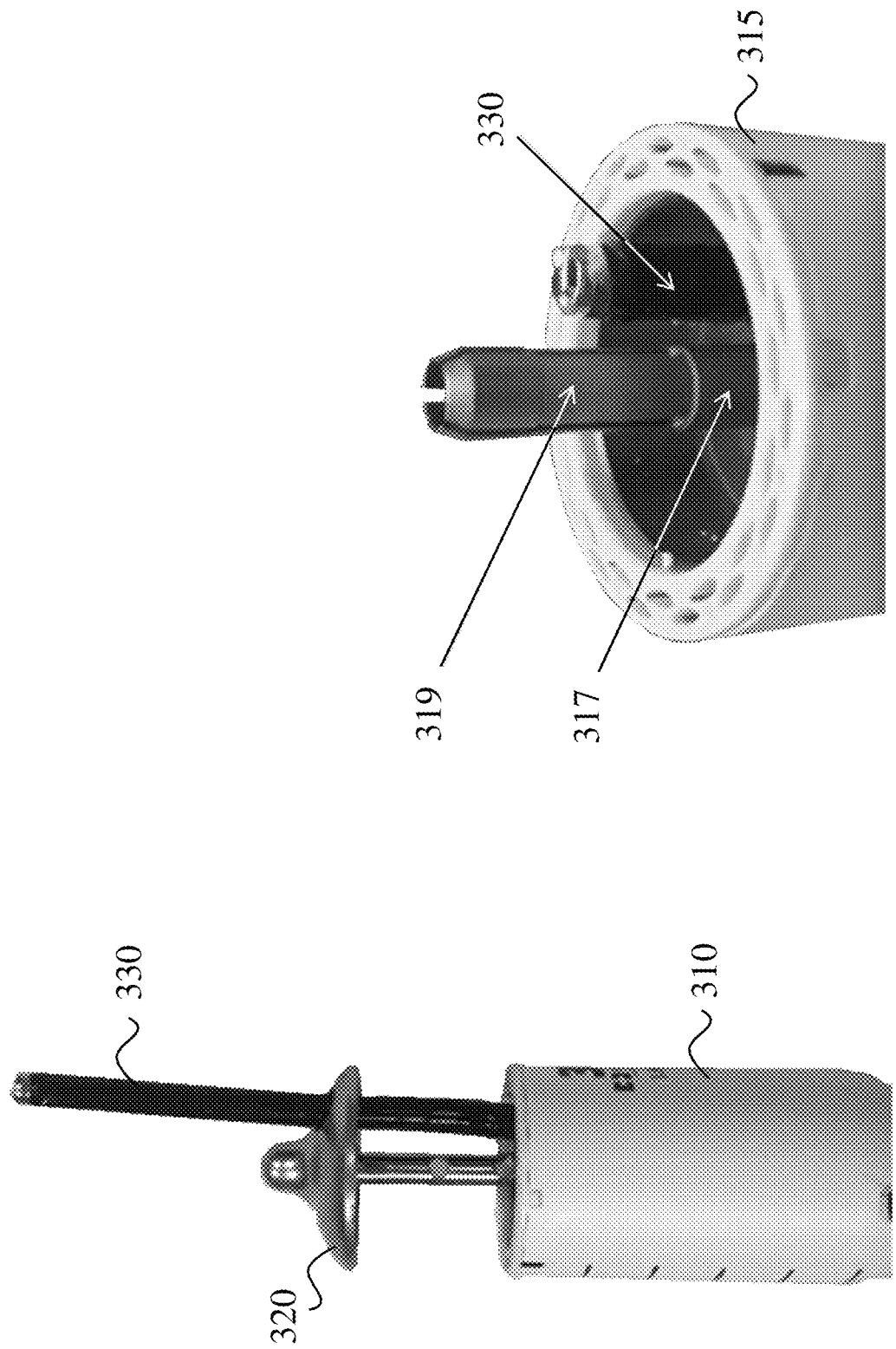
FIGS. 3A and 3B illustrate exemplary video-guided circular staplers in open positions, in accordance with embodiments of the presently disclosed technology.

FIGS. 3A and 3B illustrate examples of video-guided circular staplers in open positions in accordance with some exemplary embodiments. As shown in FIG. 3A, the anvil 320 is extended away from the shaft 310 and includes an opening offset from the center of the anvil through which the endoscope 330 may be guided. The endoscope continues through the shaft 310 of the circular stapler. The embodiment illustrated in FIG. 3A includes the anvil portion (see inset in FIG. 2) coupled to the circular stapler via the trocar (319 in FIG. 3B).

FIG. 3B illustrates a view of portion of the stapler 315 of FIG. 3A without the anvil 320 coupled. As shown therein, the inner cavity of the circular stapler in this example includes the trocar shaft 317 and the trocar 319, which enables the anvil to be coupled to the circular stapler. The depicted device further shows that the inner cavity also includes a portion of the endoscope 330, which advantageously enables the circular stapler to be guided to the target site and to enable visual examination of the stapling site after the construction of the anastomosis.

Figure 4:
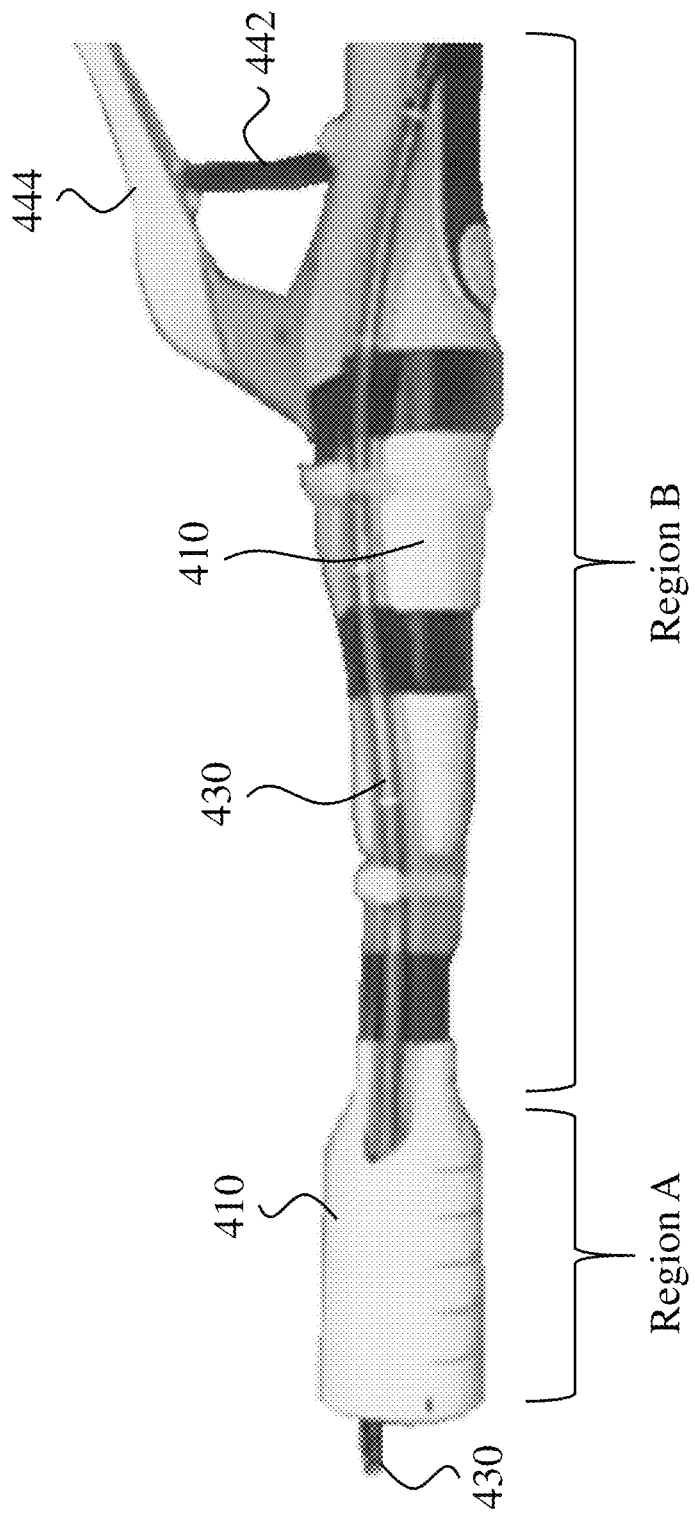
FIG. 4 illustrates an exemplary video-guided circular stapler in a closed position, in accordance with embodiments of the presently disclosed technology.

FIG. 4 illustrates an exemplary video-guided circular stapler in a closed position. As shown therein, the endoscope 430 can be fed through the shaft 410 of the stapler near where it protrudes through the anvil (indicated as region A) and may then be secured on the external part of the stapler (indicated as region B), with the stapler shaft 410 and arm 444 serving as a guideway for the endoscope. In one example, a 4-millimeter endoscope is delivered through a 6-millimeter channel that has been adapted to the arm portion of the stapler. Thus, the stapler serves as an access channel.

As shown in FIGS. 3A, 3B and 4, an existing circular stapler can be retrofit by creating an opening in the anvil and an opening in the shaft of the circular stapler, thereby resulting in embodiments of the presently disclosed technology. The embodiments described in the present document are advantageously able to very precisely deliver the stapler arm to the target and significantly increase the chances that nothing is missed along the way.

In some embodiments, any existing end-to-end anastomosis (EEA) circular stapler may be retrofitted for use with any flexible or rigid endoscope, provided that the size restriction constraints are not violated. For example, the diameter of the opening(s) in the anvil and the diameter of the shaft of the circular stapler must be greater than the diameter of the endoscope. For example, the radius of the anvil can be greater than the endoscope diameter. In other example configurations, the opening in the anvil can have different sizes or shapes as long as it preserves the integrity of the anvil. For example, the opening can be oval or rectangular shaped and can span across one section of the anvil. Thus, a modified EEA circular stapler may be used with multiple scopes (e.g., a flexible scope that is better suited to some procedures or a rigid scope when a high-definition image is required).

The embodiments of the disclosed technology may be used to facilitate an endoscopy operation that uses air or $CO_2$ gas insufflation. In one example, a section of the shaft 410 of the circular stapler is retrofitted with a stopcock (not shown in FIG. 4), which is attached to a tube that is inside the shaft of the circular stapler. In an example, the stopcock/tube configuration can advantageously provide means to deliver gas flow for the purpose of properly distending the bowel lumen so as to properly visualize the stapling process and construction of the anastomosis using the endoscope through the retrofitted anvil.

Figure 5:
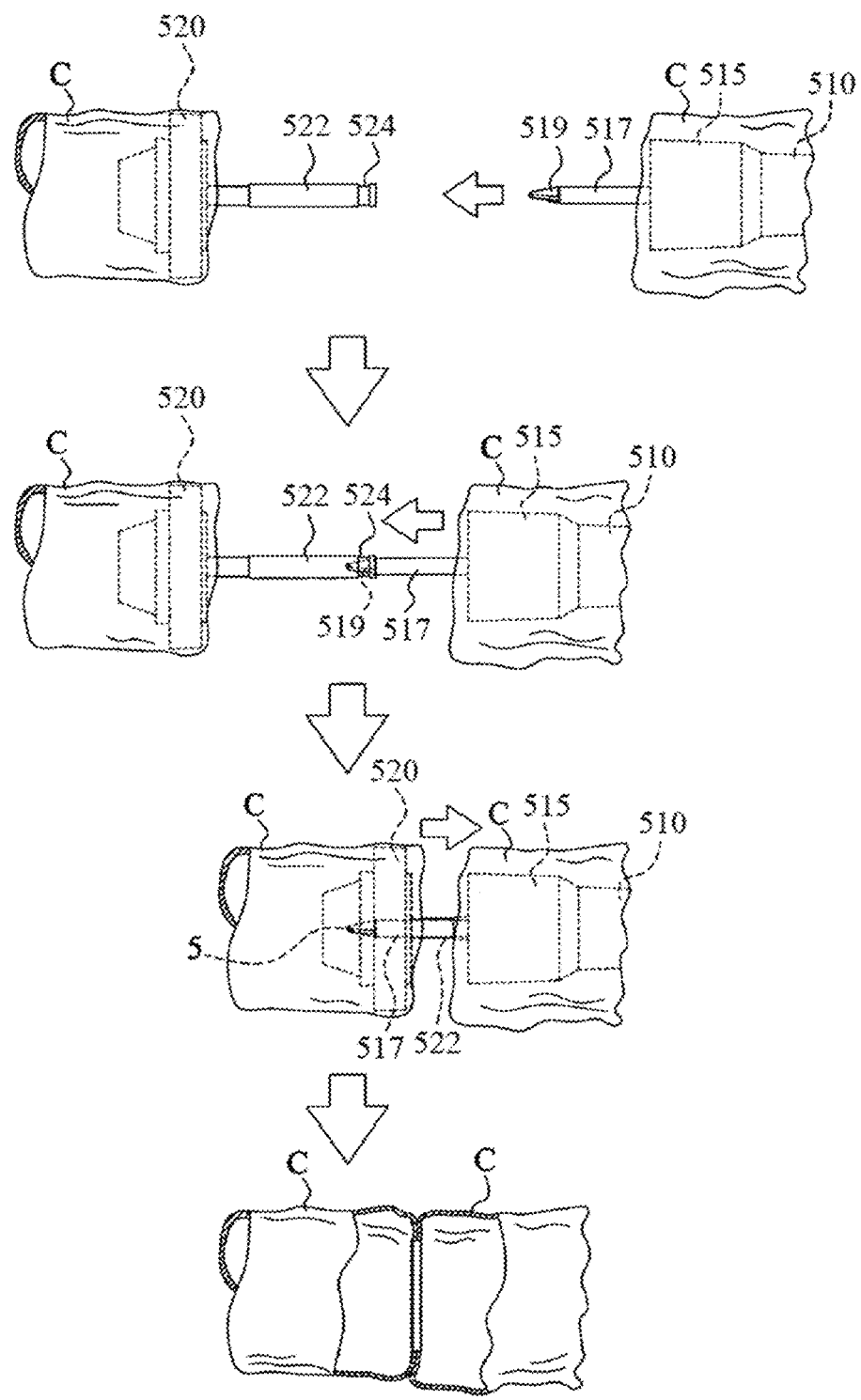
FIG. 5 illustrates an example of an end-to-end anastomosis.

FIG. 5 shows an example of an end-to-end anastomosis, which has been previously described in U.S. Patent Application No. 2010/0084453, wherein an end of an incised tract (e.g., the intestine) and the intestine's end is ready to reconnect to each other. In this example configuration, the two ends are affixed to the trocar shaft 517 and the anvil 520, respectively. As shown in FIG. 5, the anvil is connected to the anvil shaft 522. When the trocar 519 fits in the clip notch 524 of the anvil shaft 522 in position, rotating the adjusting knob (146 in FIG. 1, not shown in FIG. 5) of the circular stapler causes both tissues of intestine (C) to close.

Once the tissues are reasonably close, the circular stapler may be fired, and bolts pass through tissues of the intestine (C) into the anvil 520. Once the bolts are bent and fixed to the anvil 520, the bent bolts are used to cleave the tissues of the intestine within circumferences of the bolts. After the tissues of the intestine cleft, the circular stapler can be pulled backward along the direction of the shaft 510 through said tract of the intestine (C). The end of incised tract and the intestine's end are reconnected to form a straight passage in between, thereby completing the construction of the anastomosis.

During the example procedure described above in a rectal or rectosigmoid surgery, the anastomosis and the air leak test may have been performed successfully, but a low rectal tumor may have been missed since existing circular staplers are not equipped to enable concurrent examination. After the stapling, the stapler arm must be removed, and then an endoscope inserted to examine the procedure and the area surrounding the surgical site. Embodiments of the presently disclosed technology advantageously enable the examination to be performed concurrently with, or immediately after, the stapling procedure. In some examples, the endoscope that is inserted through the opening in the anvil may be retroflexed in order to view the stapling site from the opposite side or from multiple angles.

Figure 6A:
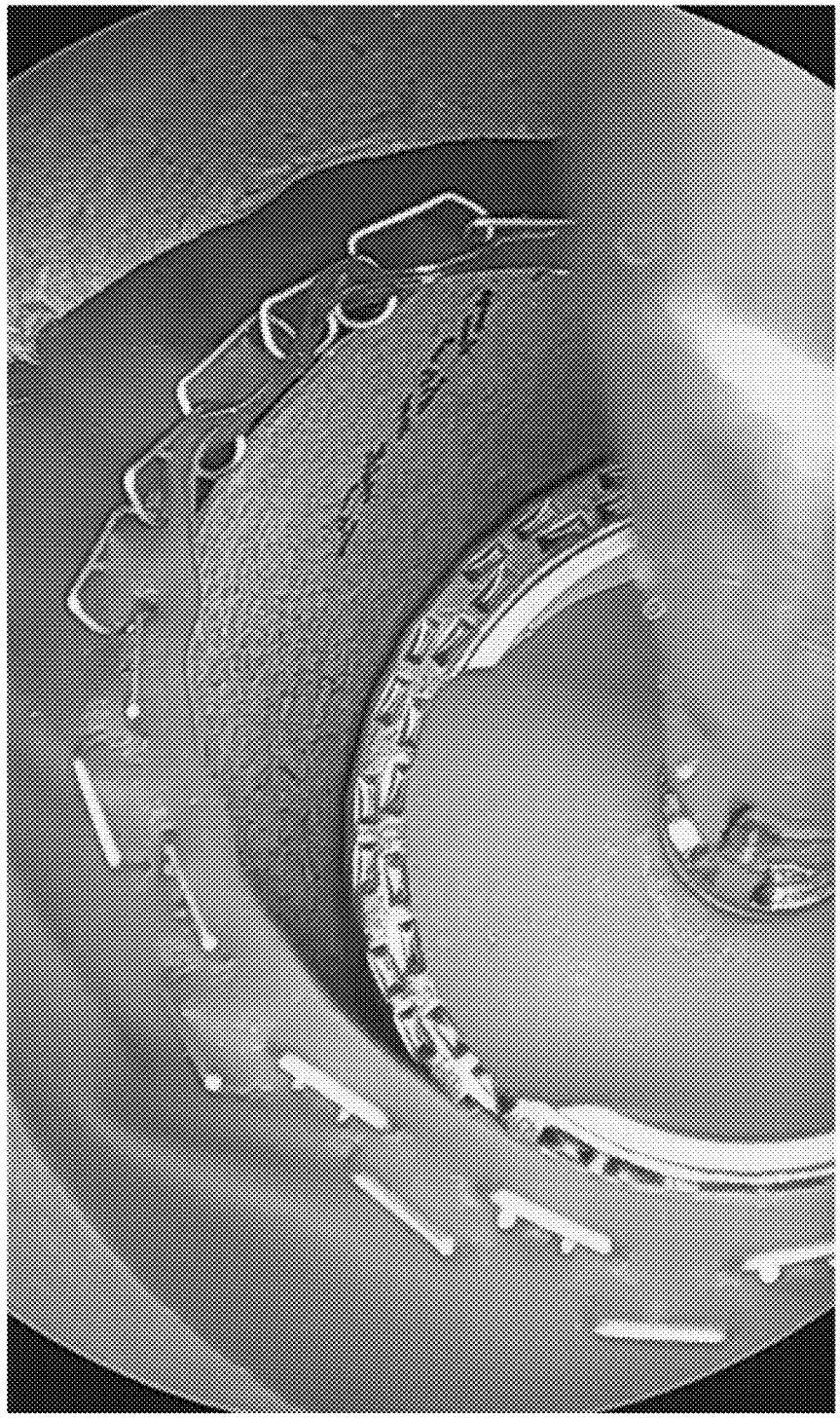
FIGS. 6A and 6B illustrate different views of the stapling site after the stapling operation by an exemplary video-guided circular stapler.
Figure 6B:
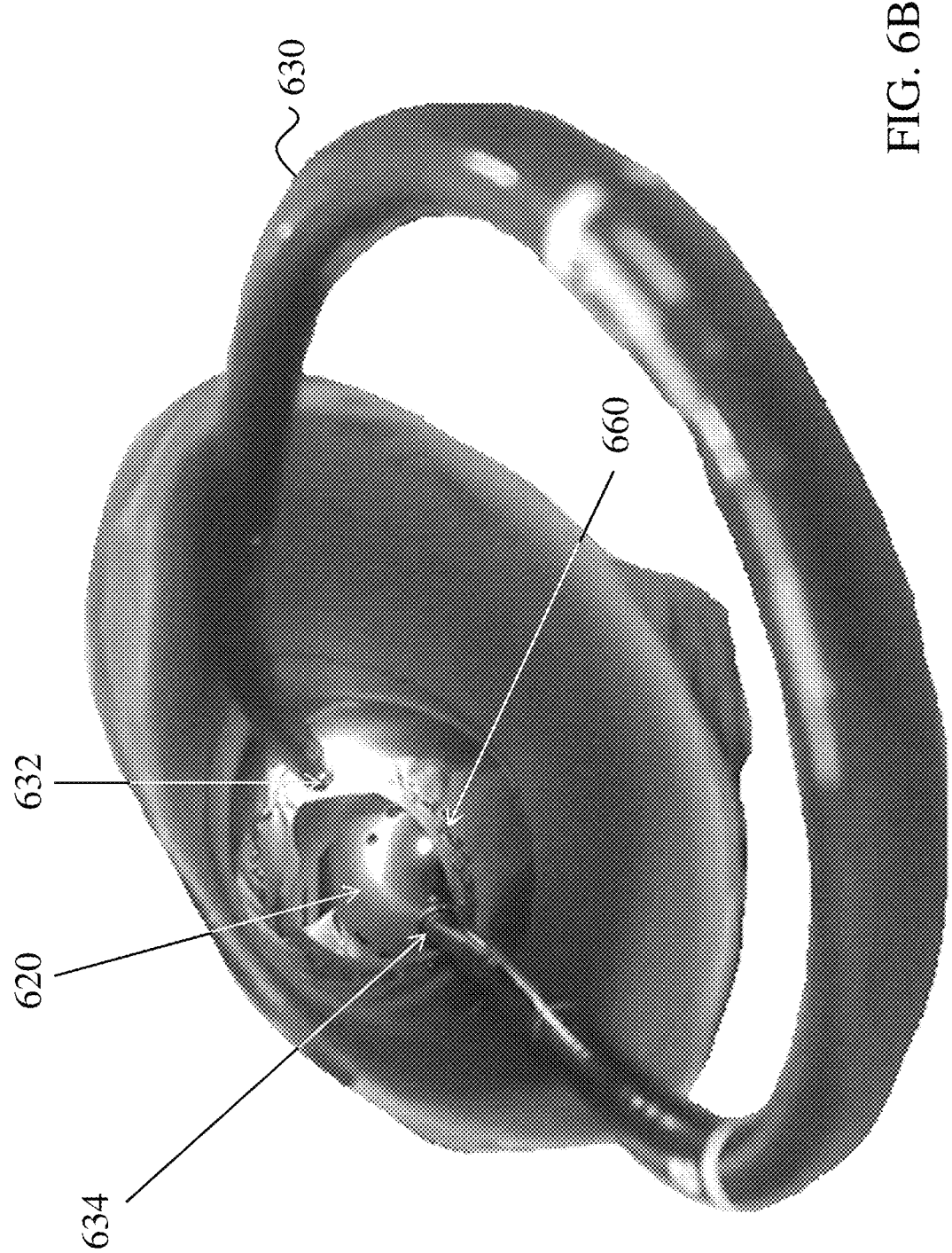

FIGS. 6A and 6B illustrate different views of the stapling site after the stapling operation is performed on a luminal by a video-guided circular stapler in accordance with some exemplary embodiments. For example, FIG. 6A illustrates an endoscopic view in which the staple line of the constructed anastomosis is clearly visible through the endoscope. The endoscopic view in FIG. 6A illustrates the rear portion of the anvil and the anvil shaft, which have moved past the stapling site. In this scenario, the endoscope may be used to examine the construction of the anastomosis, which may be subsequently manipulated using an effector arm if required.

FIG. 6B illustrates the endoscope of an exemplary video-guided circular stapler in a retroflexed position after a stapling operation in accordance with an embodiment. As illustrated in FIG. 6B, the endoscope 630 can be retroflexed so that the camera end of the endoscope 632 may be used to visualize the staple line 660 from the side opposite to the side used for entry by the circular stapler. Due to its retroflexed position, the field of view of the endoscope 630 also includes the anvil 620 and the opening 634 in the anvil (offset from the center of the anvil) through which the endoscope may be extended to guide the circular camera to the stapling site. It should be noted that due to the angle at which the images in FIGS. 6A and 6B were captured, some of the depicted surfaces and components, as well as the extent of retroflection may appear exaggerated or disproportionate. These images are intended to illustrate the underlying concepts and principles of operation.

As seen in FIGS. 6A and 6B, embodiments of the presently disclosed technology enable the completed anastomotic stapling operation to be examined right after firing the staple, and using the same instrument, instead of needing to withdraw the stapler after firing and then inserting an endoscope into the tubular region for visual examination. In another example, the video guidance provided by the embodiments described herein may assist in the construction of the anastomosis itself. It can be used to deliver the stapler arm to the target site by navigating the curves and bends with minimal trauma to the patient, then allowing the process of the construction of the anastomosis to be visualized, and finally to enabling the staple line to be manipulated, if required, using an effector arm. In some embodiments, the effector arm may be introduced through the endoscope and can be used, for example, to control bleeding or clip a small defect. Thus, embodiments of the present described technology advantageously enable medical professionals to perform the aforementioned tasks concurrently, instead of sequentially using different devices or scopes, thereby reducing the examination burden for the patient.

In yet another example, while performing an air leak test by insufflating after a previously performed anastomosis, using embodiments of the presently disclosed technology advantageously enable a visual exam to be concurrently performed, thereby providing a current examination for the patient and added revenue for the medical professional.

One of the features of the disclosed embodiments is that the endoscope can effectively operate as part of the anvil during navigation; this allows the endoscope to navigate through the organ by relaying on structural strength of the components of the circular stapler. In some implementations, the endoscope may be positioned below an outer surface of the anvil during navigation (e.g., in a retracted position or a blocked position) so to avoid contact or obstruction by the material that may be present in the surrounding environment. In implementations where the endoscope is retracted, the endoscope can be positioned at a suitable depth to still provide a sufficient field of view (FOV) to allow video capture for navigation. Furthermore, the endoscope can separate (e.g., move axially in and out) from the stapler to allow inspection of the target area pre-, post- and during the stapling procedure. Additionally, in some embodiments, the stapler may be inserted first, followed by insertion of the endoscope through a guide structure before the stapler commences its operation. The latter implementation can be beneficial in keeping the endoscope clean prior to reaching the area of interest.

Figure 7:
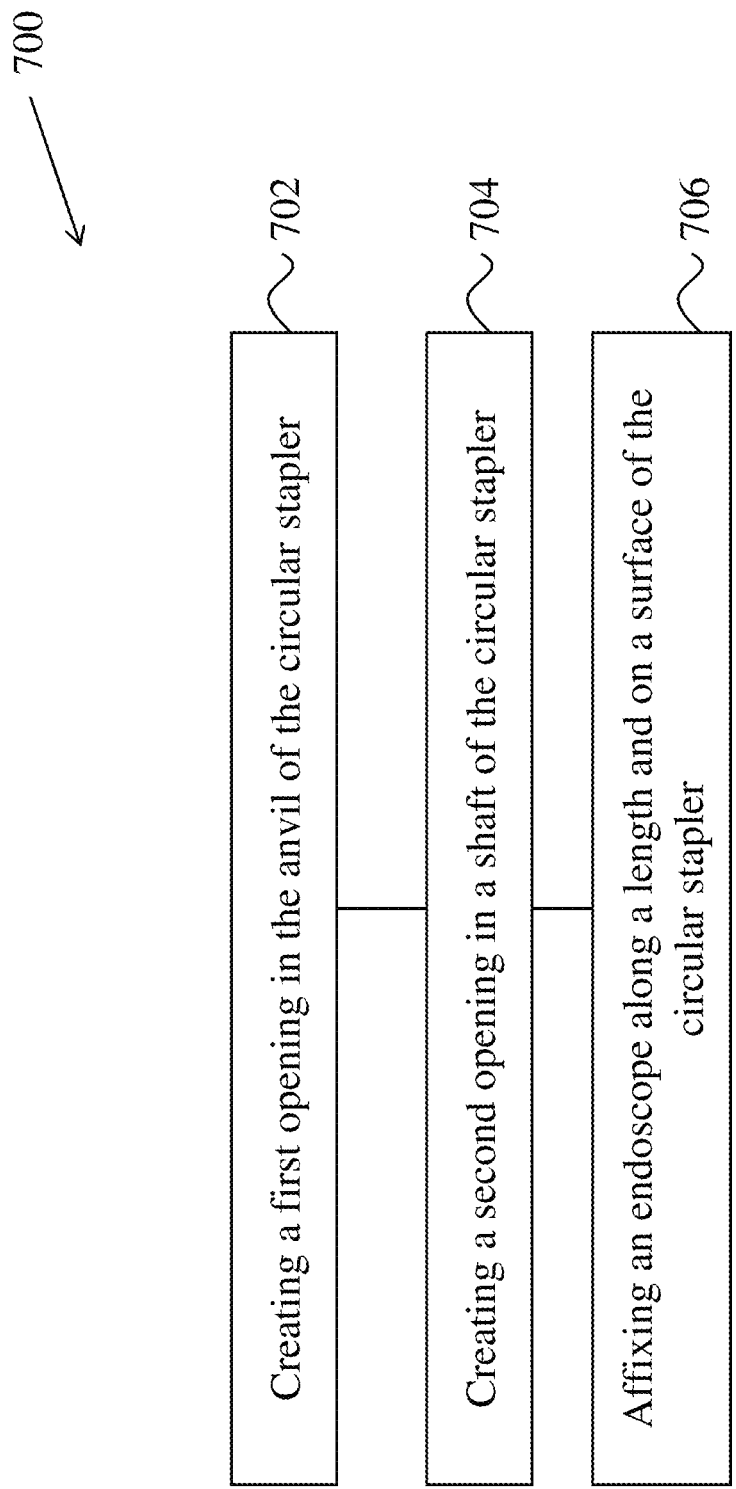
FIG. 7 illustrates a flowchart of an exemplary method for video-guided endoluminal stapling, in accordance with embodiments of the presently disclosed technology.

FIG. 7 is a flowchart of an exemplary method for producing a video-guided circular stapler. The method 700 includes, at step 702, creating a first opening in the anvil of the circular stapler. In some embodiments, the first opening is configured to allow the endoscope to transition from the internal cavity beyond an outer surface of the anvil. In some embodiments, the circular stapler is an end-to-end anastomosis (EEA) circular stapler.

The method 700 includes, at step 704, creating, a second opening in a shaft of the circular stapler. In some embodiments, the second opening is configured to allow the endoscope to transition from the surface to an internal cavity of the circular stapler.

The method 700 includes, at step 706, affixing an endoscope along a length and on a surface of the circular stapler. In some embodiments, the endoscope is affixed to the external surface of the circular stapler using one or more connectors or fasteners.

In some embodiments, the endoscope comprises a laparoscopic insufflator.

In some embodiments, the endoscope comprises an effector arm.

In some embodiments, the endoscope is (a) a flexible endoscope with the camera comprising a first resolution, or (b) a rigid endoscope with the camera comprising a second resolution that is higher than the first resolution.

Figure 8:
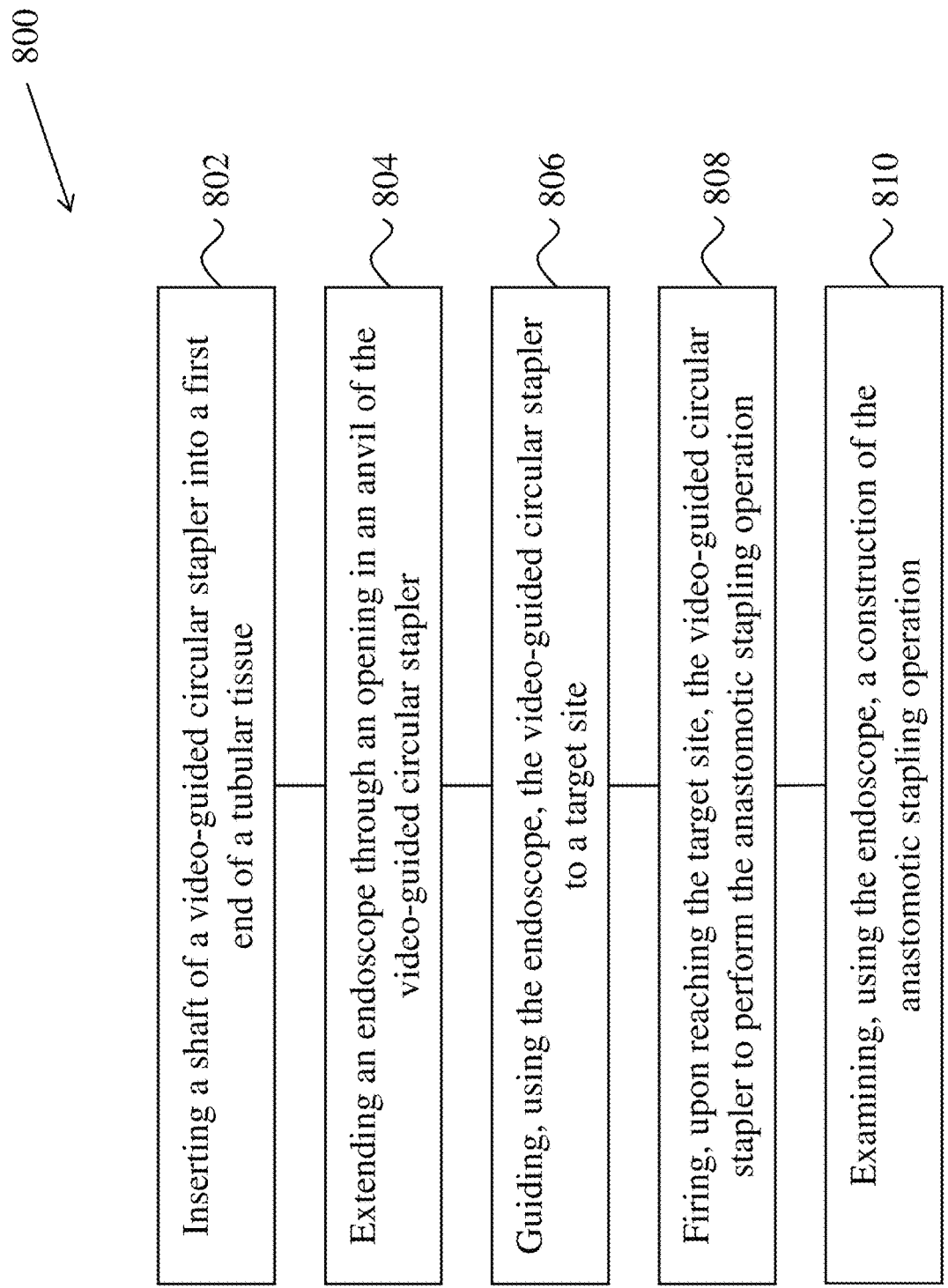
FIG. 8 illustrates a flowchart of another exemplary method for video-guided endoluminal stapling, in accordance with embodiments of the presently disclosed technology.

FIG. 8 is a flowchart of another example method for performing an anastomotic stapling operation using a video-guided circular stapler. The method 800 includes, at step 802, inserting a shaft of a video-guided circular stapler into a first end of a tubular tissue.

The method 800 includes, at step 804, extending an endoscope through an opening in an anvil of the video-guided circular stapler, the opening being offset from a center of the anvil.

The method 800 includes, at step 806, guiding, using the endoscope, the video-guided circular stapler to a target site.

The method 800 includes, at step 808, firing, upon reaching the target site, the video-guided circular stapler to perform the anastomotic stapling operation.

The method 800 includes, at step 810, examining, using the endoscope, a construction of the anastomotic stapling operation.

In some embodiments, the method 800 further includes clipping, using an effector arm in the endoscope, at least a portion of the tubular tissue adjacent to the target site. As noted previously, embodiments of the disclosed technology advantageously enable guidance of the circular stapler to a target site, the construction of the anastomosis, the visual inspection of the construction, and any clipping or manipulation, if required, using a single instrument: the video-guided endoluminal stapling system described in this patent document.

In some embodiments, the tubular tissue is a colon, a small intestine or a gastrointestinal tract, and the video-guided endoluminal stapling system may be used in a variety of procedures that include, but are not limited to, colonoscopies, gastroscopies or ureteroscopies.

Some embodiments of the present disclosed technology include a video-guided endoluminal stapling system that comprises an anvil and a shaft, an endoscope, and one or more connectors or fasteners that hold the endoscope against the shaft of the circular stapler, wherein the anvil includes a first opening in the anvil, wherein the endoscope is positioned through the first opening, wherein the one or more connectors or fasteners allow the endoscope to move longitudinally along the shaft of the circular stapler, and wherein a section of the shaft includes a second opening that allows the endoscope to transition from an external surface of the shaft to an internal cavity of the stapler.

In some embodiments, at least one of the one or more connectors or fasteners has a diameter that is less than or equal to a maximum diameter of a distal end of the circular stapler. This ensures that the circular stapler may be used with minimal trauma to the patient.

In some embodiments, the first opening is offset from a center of the anvil, and may be of any size or shape to accommodate a wide variety of endoscopes. However, the first opening must be created to maintain the integrity of the anvil.

In some embodiments, endoscope comprises a light source and a camera. In an example, the endoscope is (a) a flexible endoscope with the camera comprising a first resolution, or (b) a rigid endoscope with the camera comprising a second resolution that is higher than the first resolution. In another example, the camera is a wireless camera that uses one or more of a Bluetooth, Zigbee, Wi-Fi or Near Field Communication (NFC) technology. In other embodiments, the endoscope comprises a means for insufflation. In yet other embodiments, a head of the anvil is between 25-33 mm and a diameter of the endoscope is 2-5 mm. In an example, the head of the anvil is 29 mm and the diameter of the endoscope is 4 mm. In yet other embodiments, the endoscope comprises a laparoscopic insufflator. In yet other embodiments, the light source is a cold light source, e.g., a source for the light being outside of the endoscope and optionally equipped with a condenser system. In an example, the light is transmitted through fiber-optic light guides to minimize the heat at the tip of the endoscope. In some embodiments, the light has a color temperate that can range from 5500 K to 6500 K. In other embodiments, the light source may be a high-performance light-emitting diode (LED) or a xenon lamp.

In some embodiments, the system further includes a display, coupled to the endoscope, to display an image captured by the camera. As noted previously, the endoscope may be coupled wirelessly to the display.

In some embodiments, retrofitted or new stapling devices include video, image or camera guidance. In an example, the guidance may be provided using a flexible camera (e.g., a flexible endoscope used for colonoscopy, gastroscopy or ureteroscopy). In another example, the guidance may be provided using a rigid camera (e.g., a laparoscope with a rigid camera lens of any diameter).

Some embodiments of the present disclosed technology include a system for improving endoluminal stapling that comprises a circular stapler comprising a shaft, an endoscope, and one or more connectors, fasteners, or guides that allow the endoscope to move longitudinally along the shaft of the circular stapler, wherein a section of the shaft or a housing of the stapler comprises an opening that allows the endoscope to transition from an external surface of the shaft to an internal cavity of the stapler. In some embodiments, the endoscope includes an air or carbon dioxide ($CO_2$) insufflator.

In some embodiments, the endoscope may be guided through the entire shaft of the circular stapler, from the proximate end to the distal end. In other embodiments, the endoscope may not be positioned in an opening that is offset from the center of the anvil. In an example, the anvil can be shaped like an annulus, with an opening in the center of the anvil, through which the endoscope may pass. In another example, the anvil may have a partial opening on its edge to enable the endoscope to be passed through from the shaft of the circular stapler to beyond the outer surface of the anvil. Embodiments of the disclosed technology advantageously enable an endoscope to be guided longitudinally along the shaft of the circular stapler (either entirely within the internal cavity of the stapler, or partially inside and outside the shaft) to beyond the outer surface of the anvil in order to aid in the guidance, construction and/or examination of an anastomosis.

Figure 9:
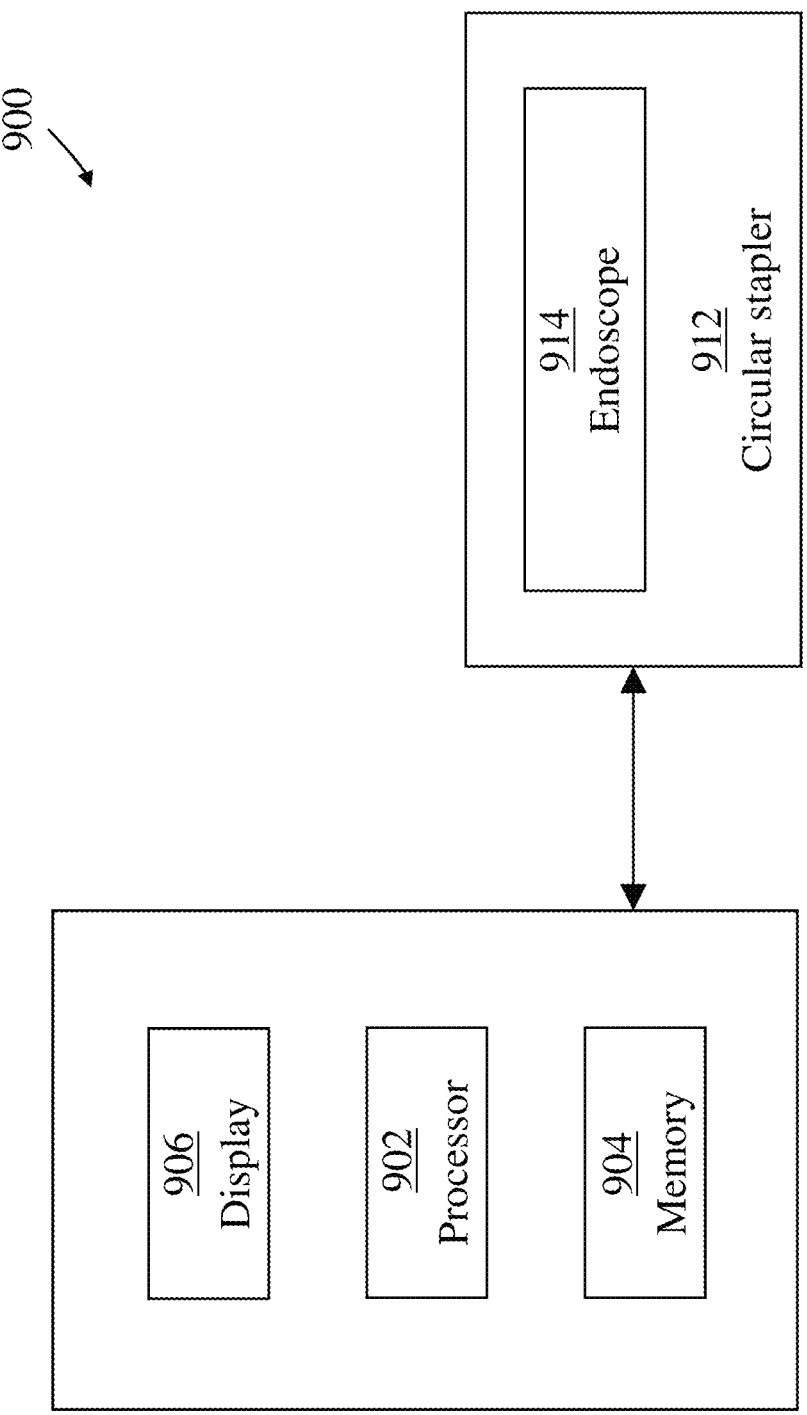
FIG. 9 illustrates a block diagram representation of an apparatus, in accordance with embodiments of the presently disclosed technology.

FIG. 9 is a block diagram of a video-guided endoluminal stapling system 900. The system 900 may be used to implement one or more of the methods described in this document. The system 900 may include one or more processors 902, one or more memories 904 and a display 906. The processor(s) 902, memory (memories) 904 and display 906 are configured to interface with a circular stapler 912 that includes an endoscope 914.

In some embodiments, the camera on the endoscope 914 may include wireless transmission capabilities (including, but not limited to, a wireless transceiver) that may use one or more of Bluetooth, Wi-Fi, Near Field Communications (NFC), Zigbee or other wireless technologies. In some embodiments, the image (or video stream) may be captured live or be recorded and may be in any format or definition including high-definition and ultra-high definition, in 2D or 3D, and projected onto a viewable monitor of any kind (e.g., display 906) including LED, LCD or plasma screen or other such device including computer-based devices.

It is intended that the specification, together with the drawings, be considered exemplary only, where exemplary means an example.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A system for improving endoluminal stapling, comprising:
   a circular stapler comprising an anvil and a shaft;
   an endoscope; and
   one or more connectors or fasteners that hold the endoscope against the shaft of the circular stapler,
   wherein the anvil comprises a first opening in the anvil, wherein the endoscope is positioned through the first opening to enable viewing a stapling site from a first direction, wherein the one or more connectors or fasteners allow the endoscope to move longitudinally along the shaft of the circular stapler, wherein a section of the shaft comprises a second opening that allows the endoscope to transition from an external surface of the shaft to an internal cavity of the stapler, and wherein the endoscope is configured to protrude through the first opening and flex back to enable viewing the stapling site from a second direction that is opposite to the first direction.

2. The system of claim 1, wherein at least one of the one or more connectors or fasteners has a diameter that is less than or equal to a maximum diameter of a distal end of the circular stapler.

3. The system of claim 1, wherein the first opening is offset from a center of the anvil.

4. The system of claim 1, wherein the endoscope comprises a light source and a camera.

5. The system of claim 4, wherein the endoscope is a flexible endoscope with the camera comprising a first resolution.

6. The system of claim 4, wherein the camera is a wireless camera that uses one or more of a Bluetooth, Zigbee, Wi-Fi or Near Field Communication (NFC) technology.

7. The system of claim 4, further comprising:
   a display, coupled to the endoscope, to display an image captured by the camera.

8. The system of claim 1, wherein the endoscope comprises a means for insufflation.

9. The system of claim 1, wherein a head of the anvil is between 25-33 mm, and wherein a diameter of the endoscope is 2-5 mm.

10. The system of claim 9, wherein the head of the anvil is 29 mm, and wherein the diameter of the endoscope is 4 mm.

11. The system of claim 1, wherein the endoscope comprises a laparoscopic insufflator.

12. The system of claim 1, wherein the endoscope comprises an air or carbon dioxide ($CO_2$) insufflator.

13. The system of claim 1, wherein the circular stapler comprises a proximal end and a distal end comprising the anvil, wherein the shaft is divided into a first region at the distal end and a second region, whose length is longer than that of the first region, at the proximal end, and wherein the second opening is in the first region.

* * * * *